United States Patent
MacMahon et al.

(10) Patent No.: US 9,901,478 B2
(45) Date of Patent: Feb. 27, 2018

(54) METHODS AND APPARATUSES FOR THE EXTERNAL DISTRACTION IN THE ASSISTANCE OF SPINAL DEFORMITIES

(71) Applicant: CHINE, LLC, Exeter, NH (US)

(72) Inventors: John MacMahon, Exeter, NH (US); Edward Brian MacMahon, Exeter, NH (US); Tom Saul, El Granada, CA (US)

(73) Assignee: Chine, LLC, Exeter, NH (US)

( * ) Notice: Subject to any disclaimer, the term of this patent is extended or adjusted under 35 U.S.C. 154(b) by 0 days.

(21) Appl. No.: 14/645,218

(22) Filed: Mar. 11, 2015

(65) Prior Publication Data

US 2015/0257915 A1    Sep. 17, 2015

Related U.S. Application Data

(60) Provisional application No. 61/950,892, filed on Mar. 11, 2014.

(51) Int. Cl.
*A61F 5/00* (2006.01)
*A61F 5/042* (2006.01)

(52) U.S. Cl.
CPC .................................. *A61F 5/042* (2013.01)

(58) Field of Classification Search
CPC .. A61F 5/02; A61F 5/024; A61F 5/026; A61F 5/04; A61F 5/042; A61F 5/048; A61B 17/025; A61B 2017/0256; A61B 2019/464; A61B 2017/00734; A61B 19/56; A61B 2017/00473; A61B 2019/5248; A61B 17/0206; A61B 17/0293; A61B 17/12136; A61B 17/86; A61B 17/885; A61B 19/081; A61B 19/26; A61B 19/2203; A61B 19/5212; A61B 2017/00477; A61B 2019/2223; A61B 2019/223; A61B 2019/2234; A61B 2019/2242; A61B 2019/2292; A61B 17/00234; A61B 5/103; A61B 5/1036; A61B 5/4561; A61B 5/4566; A61B 17/60; A61H 1/02; A61H 1/0218; A61H 1/0222; A61H 1/0229; A61H 1/0292; A61H 2201/1619; A61H 2201/1635
USPC ............... 602/32–40, 19; 128/845, 849–856, 128/870–871; 600/594
See application file for complete search history.

(56) References Cited

U.S. PATENT DOCUMENTS

| 4,085,744 A | 4/1978 | Lewis et al. |
| 4,269,178 A | 5/1981 | Keene |
| 4,409,968 A | 10/1983 | Drummond |
| 4,411,259 A | 10/1983 | Drummond |
| 4,688,558 A | 8/1987 | Hooper et al. |
| 4,763,680 A | 8/1988 | Acosta |
| 4,832,049 A | 5/1989 | Matsushita et al. |
| 4,846,194 A | 7/1989 | Sabia |

(Continued)

FOREIGN PATENT DOCUMENTS

WO    WO2014/138504 A2    9/2014

OTHER PUBLICATIONS

Carragee et al.; Spinal bracing in adolescent idiopathic scoliosis; Engl. J. Med.; 369(16); pp. 1558-1560; Oct. 17, 2013.

(Continued)

*Primary Examiner* — Tarla Patel
(74) *Attorney, Agent, or Firm* — Shay Glenn LLP

(57) ABSTRACT

Spinal distraction systems including methods of use.

9 Claims, 5 Drawing Sheets

(56) References Cited

U.S. PATENT DOCUMENTS

| | | |
|---|---|---|
| 4,854,304 A | 8/1989 | Zielke |
| 4,957,103 A | 9/1990 | Young et al. |
| 4,969,452 A | 11/1990 | Petrofsky et al. |
| 5,012,798 A | 5/1991 | Graf et al. |
| 5,045,829 A | 9/1991 | Kuramochi et al. |
| 5,053,005 A | 10/1991 | Borodic |
| 5,072,725 A | 12/1991 | Miller |
| 5,074,288 A | 12/1991 | Miller |
| 5,158,531 A | 10/1992 | Zamosky |
| 5,451,200 A | 9/1995 | LaBella et al. |
| 5,462,518 A | 10/1995 | Hatley et al. |
| 5,584,072 A | 12/1996 | Kim et al. |
| 5,599,286 A | 2/1997 | Labelle et al. |
| 5,620,009 A | 4/1997 | DePasquale |
| 5,718,670 A | 2/1998 | Bremer |
| 5,785,968 A | 7/1998 | Kimachi et al. |
| 6,082,365 A | 7/2000 | Yenin |
| 6,612,310 B2 * | 9/2003 | Sklar .................... A61B 19/081 128/849 |
| 6,757,916 B2 | 7/2004 | Mah et al. |
| 6,884,775 B1 | 4/2005 | Tabin et al. |
| 6,899,689 B1 | 5/2005 | Modglin |
| 7,197,780 B2 * | 4/2007 | Petric .................... A61G 7/0005 5/604 |
| 7,250,496 B2 | 7/2007 | Bentwich |
| 7,271,328 B2 | 9/2007 | Pangrle |
| 7,344,674 B2 | 3/2008 | Williams |
| 7,595,043 B2 | 9/2009 | Hedrick et al. |
| 7,715,605 B2 | 5/2010 | Verre et al. |
| 7,771,716 B2 | 8/2010 | Hedrick et al. |
| 7,819,904 B2 | 10/2010 | Golembiewski |
| 7,967,767 B2 | 6/2011 | Ogilvie |
| 8,012,210 B2 | 9/2011 | Lin et al. |
| 8,057,472 B2 | 11/2011 | Walker et al. |
| 8,070,777 B2 | 12/2011 | Soboleski et al. |
| 8,163,896 B1 | 4/2012 | Bentwich |
| 8,182,438 B2 | 5/2012 | Rumsey |
| 8,207,316 B1 | 6/2012 | Bentwich |
| 8,343,189 B2 | 1/2013 | Assell et al. |
| 8,367,405 B2 | 2/2013 | Gronthos et al. |
| 8,394,125 B2 | 3/2013 | Assell et al. |
| 8,784,339 B2 * | 7/2014 | Stein .................... A61B 17/885 600/587 |
| 2011/0251538 A1 | 10/2011 | Floyd |
| 2014/0039351 A1 * | 2/2014 | Mix .................... A61B 5/1114 600/587 |
| 2014/0200496 A1 | 7/2014 | Hyde et al. |
| 2015/0257678 A1 | 9/2015 | Knecht et al. |

OTHER PUBLICATIONS

Clin et al.; A biomechanical study of the charleston brace for the treatment of scoliosis; Spine; 35(19); pp. E940-E947; Sep. 1, 2010.

Weinstein et al.; Effects of bracing in adolescents with idiopathic scoliosis; N. Engl. J. Med.; 369(16); pp. 1512-1521; Oct. 17, 2013.

Zablozki et al.; The ASCO scoliosis treatment method as an alternative to bracing and surgery for idiopathic scoliosis; Archives of Physical Medicine and Rehabilitation; 84(9); pp. E15; Sep. 2003 (Poster Presentation # 54).

* cited by examiner

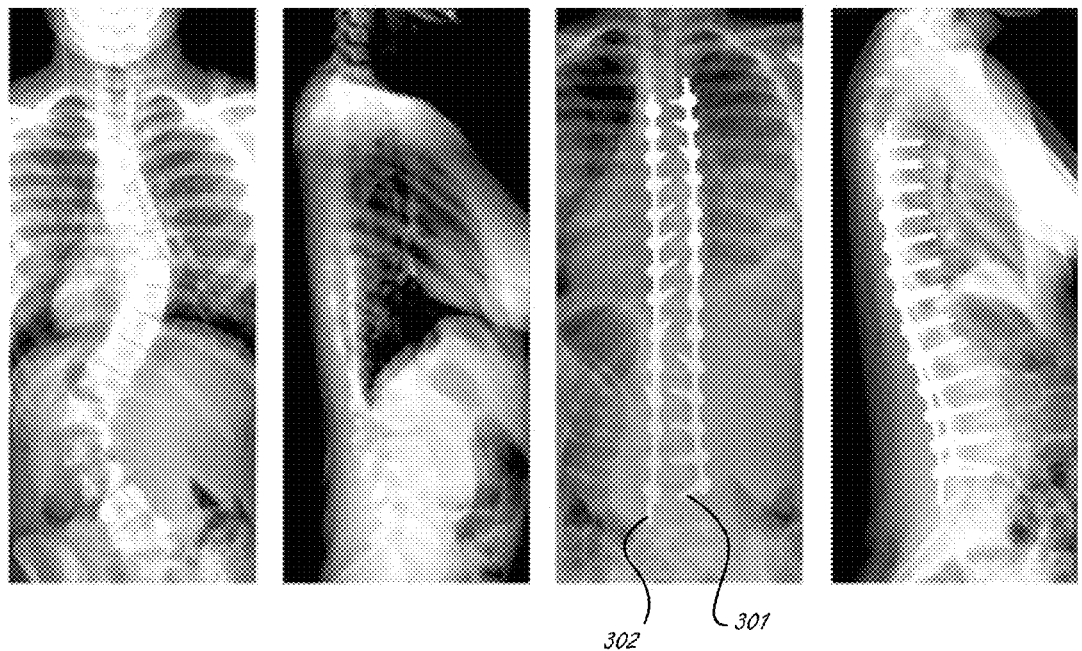
FIG. 3A PRIOR ART
FIG. 3B PRIOR ART
FIG. 3C PRIOR ART
FIG. 3D PRIOR ART
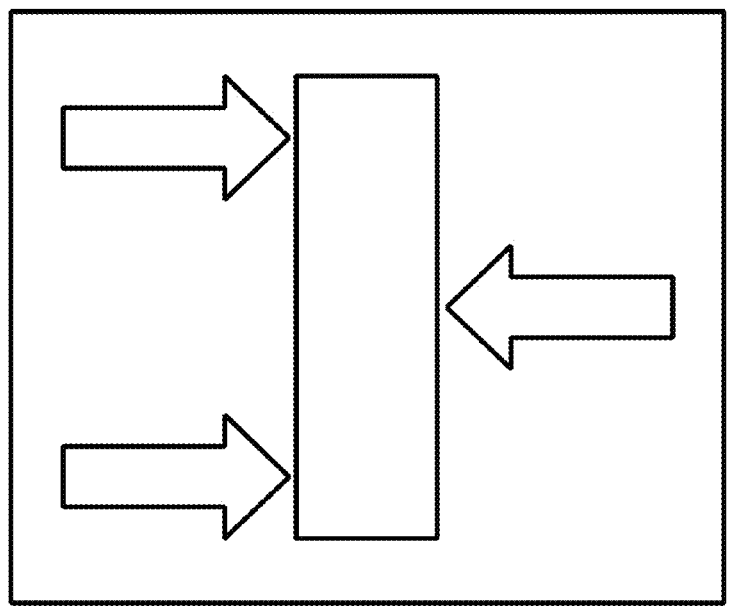
Fig. 4
PRIOR ART

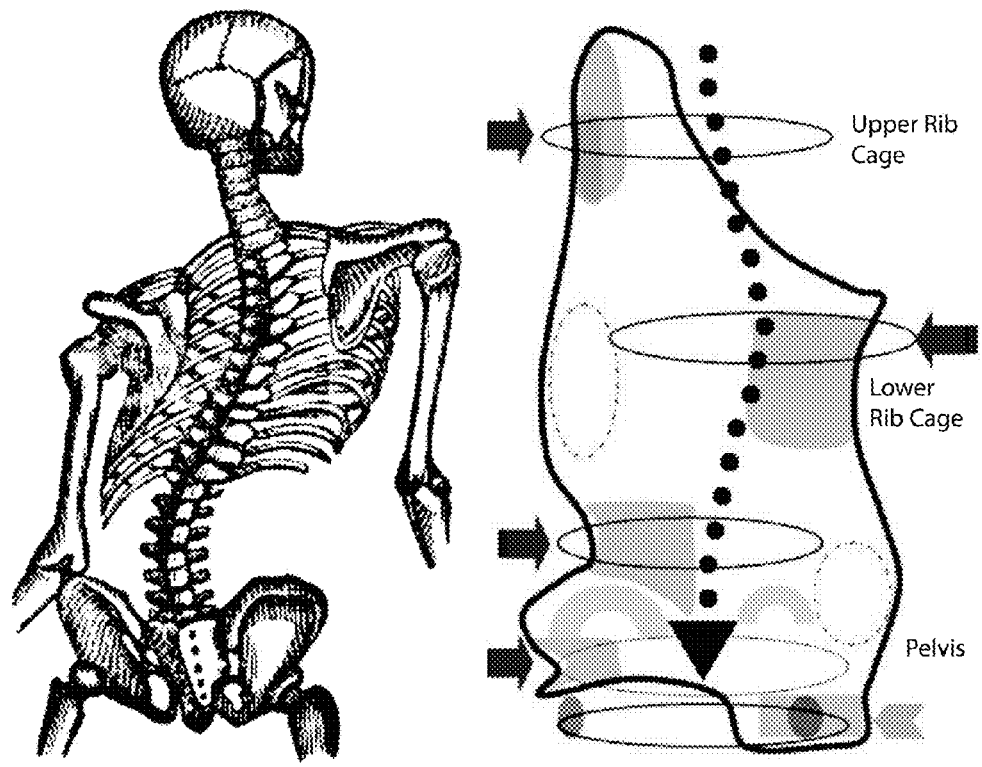
Fig. 5A
PRIOR ART
Fig. 5B
PRIOR ART
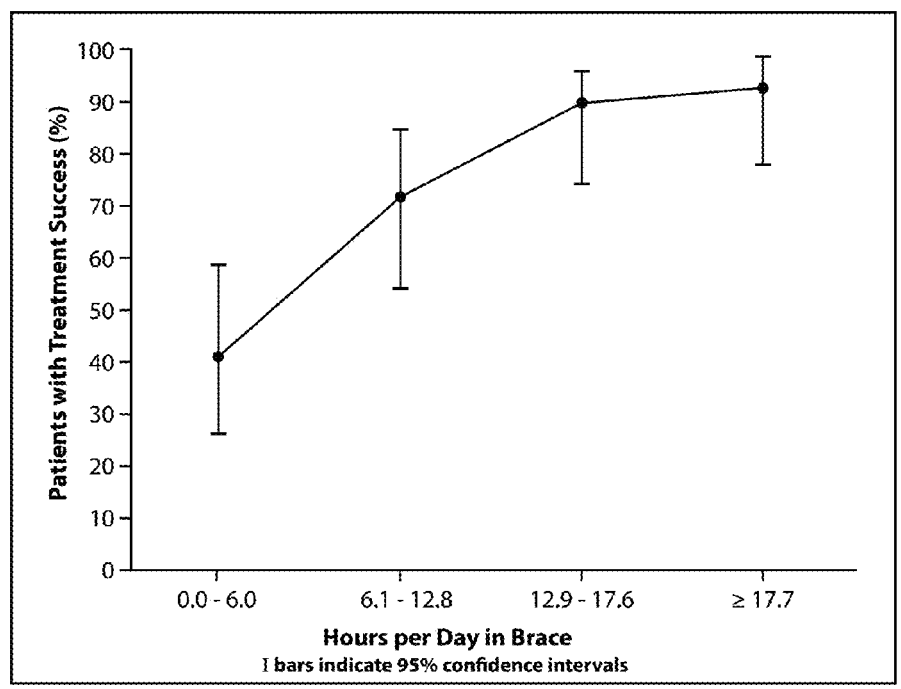
Fig. 6
PRIOR ART

Loading Waveforms for Distraction or Loading Input and Feedback

SINUSOIDAL

SAWTOOTH

RAMP PLUS SAWTOOTH

METHODS AND APPARATUSES FOR THE EXTERNAL DISTRACTION IN THE ASSISTANCE OF SPINAL DEFORMITIES

CROSS-REFERENCE TO RELATED APPLICATIONS

This application claims priority to U.S. Provisional Application No. 61/950,892, filed Mar. 11, 2014, which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The field of the invention generally relates to external methods for treating disorders of the skeletal system.

BACKGROUND OF THE INVENTION

Surgical approaches are the dominant correction for spinal deformities, in particular those associated with scoliosis. Scoliosis is a progressive condition normally affecting young women during their skeletal development. In the US it is common for all 5th grade children to be assessed for any spinal deformation. Progression from a slight spinal angle, referred to as the Cobb angle 101, to a large deformation >35 degrees 102 can occur rapidly (FIGS. 1A-1B). Significant health conditions can occur with angles greater than 70 degrees, including respiratory, neurological, and social health issues associated with the cosmetic aspects of the deformity.

Surgical approaches began in the mid-20th century and remain substantial and invasive. The initial approach involved the surgical introduction of Harrington rods anchored to hooks 201 above and below the curvature of the spine to distract the vertebrae into a more anatomically correct orientation (FIGS. 2A-2B).

Implant designs evolved and now the introduction of pedicle screws 301 in multiple vertebral bodies including those involved in the curve and then attachment of the pedicle screws to rods 302 is most common (FIGS. 3A-3D).

External approaches are effective at reducing the progression of the deformity as measured by the Cobb angle. A recent publication of a prospective randomized trial of 242 patients of the use of an external brace vs. no brace was published in the New England Journal of Medicine [NEJM, 2013 Oct. 17; 369(16):1512-21].

The study methodology included patients with Cobb angles between 20 to 40 degrees and having not developed to skeletal maturity. Effectiveness of the brace was defined as attainment of skeletal maturity without progression to 50 degrees or more of curvature, which signaled treatment success.

Braces incorporate the mechanical principles of three-point bending into their designs, where three forces are applied to an object in a direction that would tend to bend the object (FIG. 4).

A moment's effectiveness depends on its distance from the opposing force, also called the moment arm. It takes more force to close a heavy door if you push very close to the hinge than if you push on a doorknob near the edge. Translated, the applied rotational moment increases because the moment arm increases.

Designers of orthoses incorporating three- and four-point force or pressure systems seek to maximize moment arms within anatomical boundaries to achieve the largest bending moment on the spine with the smallest possible forces.

These braces provide 3-point leverage to bony anatomy about the spine (FIGS. 5A and 5B). The rib cage and the pelvis being the major bony groups which provide rigid purchase for the braces. These braces produce static pressure and are worn for hours throughout the day and night. A clear finding from the randomized study was that there was a significant positive association between hours of brace wear and rate of treatment success with >90% of patients that wore the braces for greater than 12.9 hours (FIG. 6).

In a subsequent comment also published within the NEJM, an equally important finding of this study was that so many growing children with adolescent idiopathic scoliosis "seem to do just fine with no treatment at all," said Dr. Eugene J. Carragee and Dr. Ronald A. Lehman Jr., "the bracing indications described are probably too broad, resulting in what may be unnecessary treatment for many patients," Dr. Carragee and Dr. Lehman said. Although there do not appear to be physiological side effects to bracing in adolescent idiopathic scoliosis, "it carries financial, emotional, and social burdens that need to be considered." They also cited that 48% of the untreated patients had a successful outcome, as did 41% of the patients with braces.

Since these patients are predominantly school-aged girls and compliance is directly correlated to outcome therein lies the clinical need for shorter duration, effective therapy that can equal or surpass these results of these present braces. Some braces try to address this by prescribing them to only be worn at night, such as the Charleston Bending Brace, which has an added benefit of being engaged while the muscles surrounding the spine are relaxed and attempts to provide a correcting force (Clin et al., Spine 2010 Sep. 1; 35(19):E940-7). The paraspinal muscles are engaged while standing and relax when lying down. The philosophy for this brace includes the supposition of biomechanical advantage that wearing a brace while these muscles are relaxed can produce an equivalent benefit in shorter duration than the upright day time braces. To date while there have been no randomized studies to confirm the clinical performance of these braces to one another, observational studies show similar results from long hours in a day time brace when compared to shorter hours in night time braces.

While the surgical approach is an option in the United States, the waiting list in other countries with socialized medicine can be as long as 18 months. In these countries and communities, a non-surgical option may be a valuable medical and economic alternative to not only limit Cobb and progression but potentially reverse its course.

SUMMARY OF THE DISCLOSURE

This disclosure addresses a need for a more efficient, dynamic distraction method and apparatus for these patients by introducing dynamic loading and leveraged anatomical distraction to not only increase the effectiveness of these static braces in their efforts and to not only slow the increase in Cobb angles, but to provide a therapy to reduce Cobb angles without surgical implants.

We assessed the biomechanical and anatomical features available to include in our design and isolated a number of them in one of our preferred embodiments. The shoulder girdle is the muscles and bones of the shoulder that when activated can provide support for the whole body. If one envisions someone on a pair of crutches, they can activate their shoulder girdle to hold up the rest of their body while swinging on their crutches. The load during someone swinging on their crutches is close to ½ a bodyweight per crutch. Relaxation of these muscles can be envisioned in the instance where one is standing on their feet and then leans on a pair of crutches, their shoulders are relaxed and the soft tissues of the shoulder girdle relax. In that state there is negligible load on the crutches with the shoulder relaxed and the patient standing on their legs.

The shoulder girdle is an important concept in this invention. So we will delve one layer further into its anatomical and biomechanical importance. Referring back to the Harrington rods in surgical therapy for scoliosis, the rods are attached to hooks which are fixed to the patients vertebrae. From a biomechanical viewpoint the rod is the centerline of the vertebral column and the length from the rod to the apex of the curve is the lever arm available for a Harrington rod. Experimentally surgeons limit the tension and compression in the fixation of these rods to ½ the patient's bodyweight. This is the maximum load that the hook and vertebral body can support. If we look at the mechanical moment about that anchor it is ½ a bodyweight times the distance of ½ a vertebrae.

We note that an activated shoulder girdle during two-legged swing gate and the Harrington rods both are tuned for ½ a bodyweight. The lever arm though is quite different. As a means of approximation the vertebral body is about 5 cm wide and the shoulder girdle 30 cm wide. The ratio then is the difference in available torque. An activated shoulder girdle offers a greater than 5 fold leverage advantage.

Additionally we target two other biomechanical advantages—first we will target the relaxed phase of paraspinal muscles. While we can train these muscles to relax and do not eliminate its potential as an embodiment, in the first embodiment described we will cyclically distract the patient while they are lying down and the normal musculature is relaxed. This will impart more of the loading and torque for distraction to the spine and not be opposed by activated paraspinal muscles.

In this first embodiment—load is delivered in a cyclical form for a time no more than a few hours. The load is anticipated to be on the order of ½ a bodyweight with the load coming up from 0 to this load in the approximately 3 seconds and a hold phase as an option before the load is reduced again and cycled. The total 0 to ½ body weight to 0 cycle time may be of many ranges but is initially targeting less than 10 seconds total.

In this first embodiment electrical drive motors apply the forces and feedback on loading is provided by integrated load cells. In this embodiment the loads are primarily aligned with the table.

In this first embodiment leverage can also be applied by independent motion of the actuators. The shoulder girdle is activated on both sides—with the actuator on the convex side is fixed and then the actuator on the concave side is loaded and works as a fulcrum to provide double the leveraged distraction on the spinal centerline.

The cyclical loading is an active means of increasing plasticity in materials and dynamic muscular and spinal stretching in an efficient means of improving flexibility. The incorporation of an active shoulder girdle provides anatomic and biomechanical leverage and leveraged distraction to optimize effectiveness and provides the promise of reduce use time to increase compliance. It is also relevant to have the loading across a broader range of soft tissues as the fundamental underlying asymmetry in idiopathic scoliosis is not well documented. Engaging the shoulder girdle will offer a dynamic leverage of the spine as well as the soft tissues throughout the upper torso.

In another embodiment, the feedback from the displacement and the force transducers, load cells, can be incorporated to provide additional insight and feedback for the patient. As used herein "patient" can also include a third party assisting in the procedure. For example, with the shoulder girdle activated the isometric contraction of either side can be presented, visually or audibly, to the patient or trainer, for feedback and incentive to the parties involved. While the structural support and muscles are implicated in the skeletal imbalance, isometric contractions and their feedback can glean qualitative and quantitative indications of their conditions and their asymmetry. The embodiment may provide for asymmetric leveraged contractions for strength and symmetry interrogation as well as leveraged distraction by maintaining one side fixed and cycling a force over distance, as well as having the patient provide compression with muscular contractions while the load sensors follow the contraction. With patient awareness and feedback, the patient can be a more active member of their therapy and thereby result in potentially more compliance and better results.

These embodiments and the reasonable combinations of them can be engendered in devices available for both the physician setting and the home care setting. The electronic transfer of data is also a reasonable internal design sufficient to provide quick response on management on progress and compliance both considerations are well-documented to be key to efficient and effective therapy.

The following U.S. patents, which are incorporated by reference herein, describe some earlier approaches, none of which engaged dynamic, cyclical loading, nor engaged an active shoulder girdle for the leverage: U.S. Pat. Nos. 8,394,125; 8,367,405; 8,343,189; 8,207,316; 8,163,896; 8,012,210; 7,967,767; 7,771,716; 7,595,043; 7,250,496; 6,884,775; 5,718,670; 5,599,286; 5,451,200; 5,158,531; 5,012,798; 4,957,103; and 4,688,558.

The following U.S. patents, which are incorporated by reference herein, describe some approaches, none of which reference dynamic cyclical loading: U.S. Pat. Nos. 8,182,438; 7,967,767; 7,344,674; 6,899,689; 5,718,670; 5,599,286; 5,584,072; 5,451,200; 5,158,531; 5,074,288; 5,072,725; 5,012,798; 4,969,452; and 4,957,103.

The following U.S. patents, which are incorporated by reference herein, describe some implantable approaches: U.S. Pat. Nos. 8,419,734; 8,057,472; 4,854,304; 4,411,259; 4,409,968; 4,269,178; and 4,085,744.

U.S. Pat. No. 4,763,680, which is incorporated by reference herein, describes a curved crutch modified for assisted walking for patients with spinal curvatures that make straight crutches a poor fit. This patent fails to disclose distraction, nor is it considered a therapy.

U.S. Pat. No. 6,082,365 provides a table for positioning the patient, addresses scoliosis, and is intended to work externally. Its mechanism of action is to vibrate the patient at high frequency while the patient is relaxed. It teaches a benefit for performing low frequency vibro-influence on the spine. Low-frequency is deemed 10-50 Hz and amplitude of the waves is 10-50 mm. The body can be in tension or not in tension.

The following U.S. patents, which are incorporated by reference herein: U.S. Pat. Nos. 8,070,777; 7,819,904; 7,271,328; 6,082,365; 5,785,968; 5,053,005; and 4,846,194.

In a poster presentation which includes Yenin as a co-author, a retrospective review of 13 patients treated with the ASCO therapy, reported results that the key component is the muscular relaxation via vibration. This mechanism of action is not present in this disclosure (Archives of Physical Medicine and Rehabilitation 84-9, Page E15, September 2003).

The following patents are also incorporated by reference herein: U.S. Pat. Nos. 5,462,518; 4,832,049; 5,620,009; and 7,715,605.

One of the key aspects of this disclosure involves external structural support with cyclical distraction during active shoulder girdle support. Additionally, the leveraged distraction provided by an external system is also novel in the treatment of spinal disorders. Additionally, the visual feedback available to the patient of loading and distraction can also greatly impact the experience and compliance. Lastly, the opportunity to provide the above novel features in either a horizontal of supine position offers the option to provide these therapies in a mode with the paraspinal muscles naturally relaxed.

BRIEF DESCRIPTION OF THE DRAWINGS

FIGS. 3A, 3B, 3C and 3D illustrate pedicle screws implanted in multiple vertebral bodies including those involved in the curve and then attachment of the pedicle screws to rods.

FIG. 4 illustrates the mechanical principles of three-point bending into their designs, where three forces are applied to an object in a direction that would tend to bend the object.

FIGS. 5A and 5B illustrate 3-point leverage to bony anatomy about the spine.

FIG. 6 illustrates a significant positive association between hours of brace wear and rate of treatment success with >90% of patients that wore the braces for greater than 12.9 hours.

DETAILED DESCRIPTION

Figure 1A:
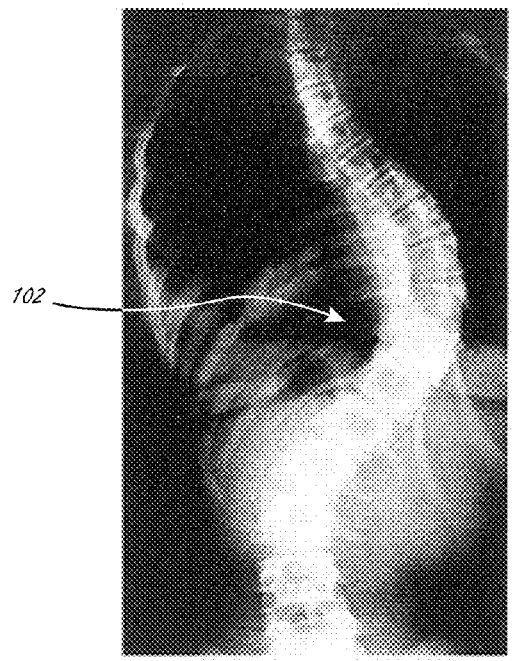
FIGS. 1A and 1B illustrate progression from a slight spinal angle, referred to as the Cobb angle, to a large deformation more than 35 degrees.
Figure 1B:
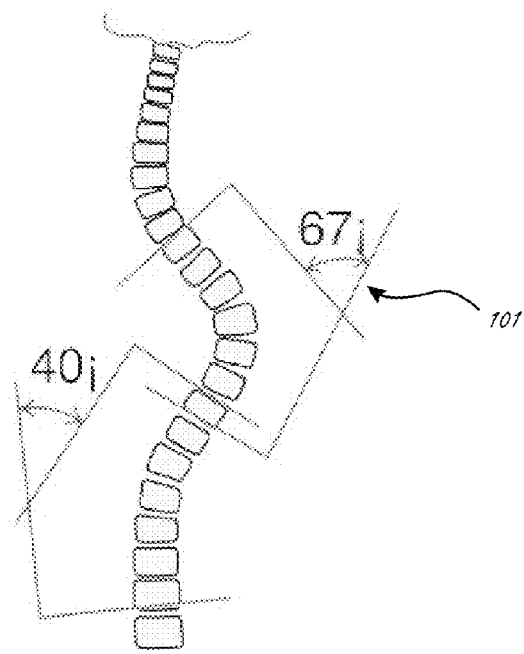
Figure 2A:
FIGS. 2A and 2B illustrate Harrington rods anchored to hooks.
Figure 2B:
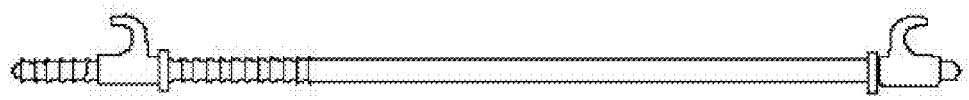
Figure 7:
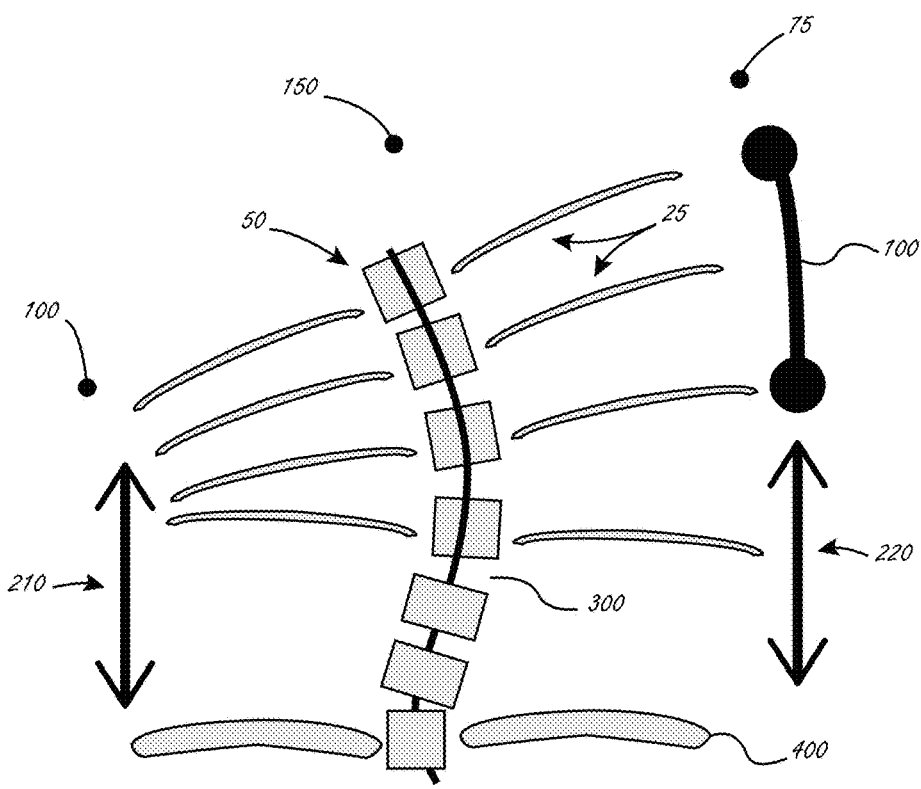
FIG. 7 illustrates a skeletal outline of a scoliosis patient.

In FIG. 7, the skeletal outline of a scoliosis patient is presented in cartoon emphasizing the anatomy and points of action for one embodiment. The vertebrae 25 and the vertebrae with ribs 50 are joined with the shoulders 100 to make the shoulder girdle 150. When the muscles of the shoulder are activated this provides for the shoulder girdle 150 to act as a unit as previously referenced. When a cyclical loading vector is provided between the pelvis 400 and the shoulder girdle 150. One can think of numerous straps and supports for fixation of the force against the pelvis 400, to help visualize an anchor for the shoulder girdle 150 imagine a crutch within each arm pits 75 but not exclusive to only these points, now there are two points of actuation for a distraction vector can be applied 210 and 220 between the pelvis and the shoulder girdle. Additionally the cartoon includes a reference point 300, with a spinal deformity Cobb angle, vertebrae near the bottom of the shoulder girdle. This reference point 300 also sees a large torque moment to reduce this Cobb angle. Of course this reference point may be throughout the spine and is cited at this level of the spine only for visualization and not an exclusive location of moment nor of Cobb angle.

Additionally, in FIG. 7 let us review the case where the shoulder on the right 100 is anchored against its anchor within its armpit 75. Then a left side load 210 is applied and then distracted by translation only on the left 210. This will produce leveraged distraction which will produce an approximate distraction force of twice the loading force on the left at the reference point 300. This is an approximated value considering the spine is midway between the two armpits 75 and then the force is applied a distance two times the midline of the reference point 300.

Additionally as the clinical presentation may include multiple curves other embodiments may include distraction in 3 dimensions with multiple tracks and angles. Additionally, as anyone familiar in the art of delivery of loads over distances may recognize, loads may be delivered by but not limited to electric, pneumatic, hydraulic or toroidal forces. Additionally, embodiments where the shoulder girdle distraction force translation is both sides at once additionally one can control one side to distract further or to a higher force independent of the other side to help isolate curves within the patients anatomy.

Figure 8:
FIG. 8 illustrates cyclical loading that can incorporate a number of waveforms with displacement or loading feedback for parameters.
Figure 8:
Figure 8:

The cyclical loading can also incorporate a number of waveforms with displacement or loading feedback for parameters (FIG. 8). Sinusoidal, saw tooth, or delta function wave forms are possible but not the exclusive forms of loading. Combinations of feedback for waveforms, displacement and loading are also envisioned and disclosed.

Figure 9:
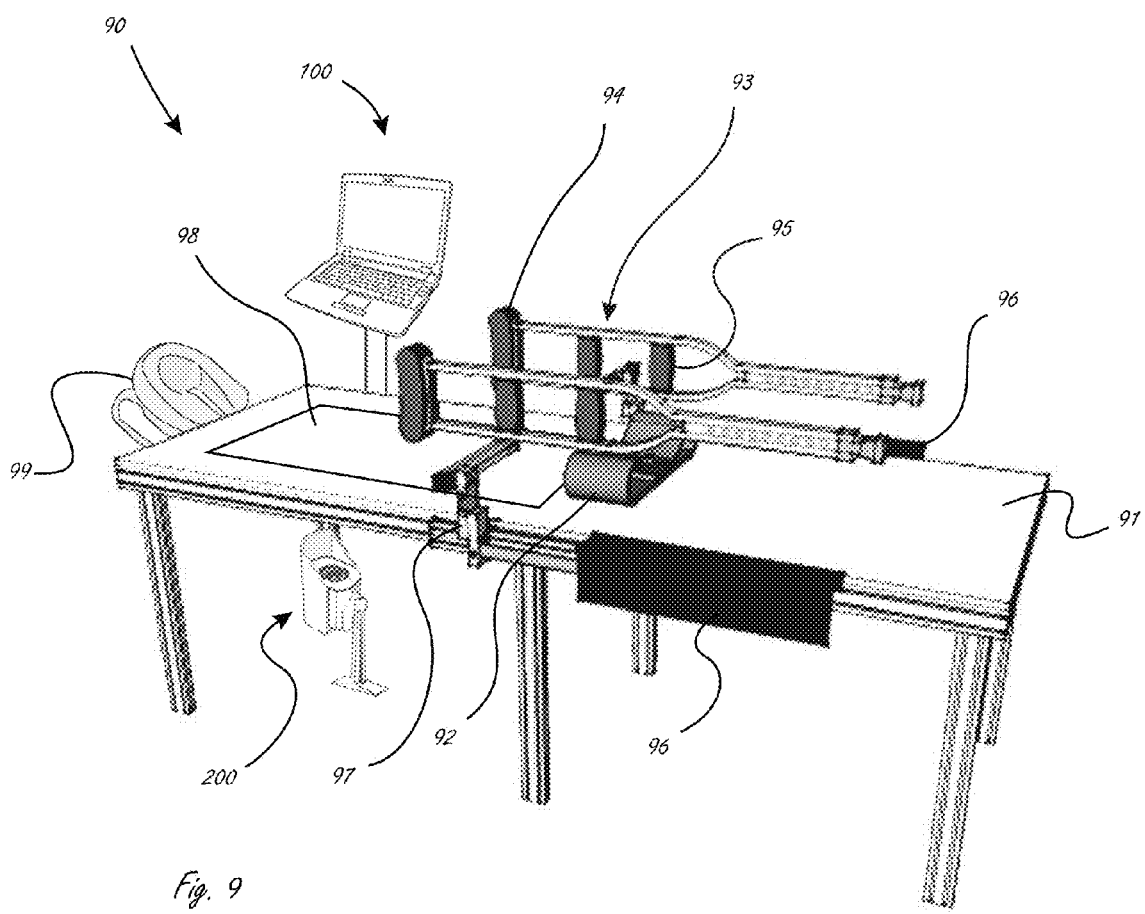
FIG. 9 illustrates a distraction system capable of providing dynamic distraction to a patient's spine.

Illustrated in FIG. 9 is a distraction system 90 capable of providing dynamic distraction to a patient's spine. The distraction system is comprised of the following elements: a table or patient support structure 91, a patient anchoring belt 92, a distractor patient interface 93, a distractor drive means 96, a distractor sensor system 97, a spinal viewing port 98. As illustrated the table has an optional face pillow 99, which allows for use of the distractor structure with the patient in a prone position or a supine position. As illustrated the system is interfaced to a monitor and/or controller 100. Also shown is optional imaging system 200.

The distractor patient interface 93 as illustrated comprises a shoulder interface 94 configured to interface with a patient's arm pit, a hand interface 95 for gripping by the patient. Alternative interfaces 93 may comprise only a grip, or only a shoulder pad, or any other form positive interface to a patients arm or shoulder such as a strapped on splint.

As illustrated there are two distractor drive mechanisms 96, one for each distracter interface. The distracter drive means as shown is comprised of a stepper driven linear actuator, any suitable mechanism such hydraulic motor and piston can be substituted. Interfaced in the drive train of the distractor mechanism is a sensor system 97 comprising a load cell for monitoring the compression and or tension transferred to the patient by the distraction system. Some embodiments will also comprise a torsional load cell.

The controller 100 provides control of the distracter drive mechanisms. Drive control can be open loop and comprise predetermined cyclical displacements of the distracter interfaces. In alternate embodiments the controller may work in a closed loop configuration where feedback (e.g., feedback from the load cells, camera, etc.) is provided to the controller. In such embodiments the feedback may be displacement, load, or quantities derived therefrom such as rates of change, or some aspect of the change in spinal configuration such as change or a reduction in Cobb angle. When load is used as the feedback source, cyclical force comprising but not limited to the waveforms as described in FIG. 8 may be applied. The curves of FIG. 8 may also represent displacements describing motions of the distractor when driven in the cyclical displacement mode.

Visualization system 200 can comprise a 2D or 3D camera for monitoring changes in spinal configuration resulting from interaction with the distraction system. When using a 2D camera a shirt with markers may be worn to help highlight changes in spinal configuration. Alternatively markers may be applied to the patient's back. When a 3D camera is used the contour of the surface of the back may be monitored and information about spinal configuration may be derived from such contours. In any of these configurations feedback to the user may be provided in the form of an actual visual image, such as shown on the display of controller 100 or other visual display monitor, of the back or a derived characteristic indicative of a change in spinal configuration such as Cobb angle. 3D cameras may use any of the technology including ultrasound, optical, or other.

In an alternate embodiment not shown an electrical impedance tomography (EIT) map of the spine may be captured during an exercise session on the system. Such a system would comprise a belt or vest incorporating one or more rings of electrodes configured as an EIT input interfaced to the controller or other processing system. One system useful for generating such images is the "EIT Pioneer Set" produced and supplied by Swisstom AG.

Visual information associated with cameras or EIT when presented to the user allows the user to refine the ways in which they interact with the system to improve the reduction in Cobb angle resulting from the interaction. Alternatively the information can be provided to the controller as an input in a control algorithm.

In some embodiments information regarding user generated loads, when the system is used in displacement mode or displacements, when the system is used in load mode, may also be presented to the user as a feedback means. Such information may be presented in the form of actual load or displacement, or a derived value such as a variation from some goal.

In an alternate embodiment, not shown, the distraction support structure may be configured as a chair such as the Dolphin massage chair.

In alternative uses, the spinal distraction systems herein can additionally be used to treat lower back pain, which may be a separate treatment, or in some embodiments it can occur in conjunction with treating spinal deformities.

As used herein spinal posture can be used interchangeably with spinal configuration.

What is claimed is:

1. A non-surgical spinal distraction system, comprising:
a patient support structure;
a first patient distractor interface secured on a first side of the patient support structure and a second patient distractor interface secured on a second side of the patient support structure, the first and second patient distractor interfaces comprising first and second, respectively, hand interface grips positioned relative to the patient support structure so a patient can grip the hand interface grips when supported by the patient support structure, the hand interface grips disposed relative to the patient support structure and configured so that a patient can apply loading vectors on the hand interface grips between the pelvis and the shoulder when the patient is supported by the patient support structure;
a patient anchoring belt adapted and configured to anchor a portion of the patient relative to the patient support structure;
a first sensor operatively coupled to the first patient distractor interface and adapted to sense the patient generated loading vectors on the first hand interface grip between the pelvis and the shoulder, the first sensor spaced from the first hand interface grip to allow a patient to apply the loading vector on the first hand interface grip between the pelvis and the shoulder without directly contacting the first sensor;
a second sensor operatively coupled to the second patient distractor interface and adapted to sense the patient generated loading vector on the second hand interface grip between the pelvis and the shoulder, the second sensor spaced from the second hand interface grip to allow a patient to apply the loading vectors on the second hand interface grip between the pelvis and the shoulder without directly contacting the second sensor;
a camera secured relative to the patient support structure such that when the patient is supported by the patient support structure, the camera is in position to capture an image of the patient's back;
a controller adapted to receive information indicative of the captured image; and
a monitor in communication with the controller, the monitor adapted to provide visualizing of the patient's back based on the image captured by the camera.

2. The system of claim 1, wherein the controller is further adapted to control movement of at least one of the first and second patient distractor interfaces.

3. The system of claim 2, wherein the controller is further adapted to control movement of the at least one of the first and second patient distractor interfaces based on the sensed patient generated loading vectors.

4. The system of claim 1 wherein the patient support structure includes a horizontal surface.

5. A non-surgical spinal distraction system, comprising:
a patient support structure;
a first patient distractor interface secured on a first side of the patient support structure and a second patient distractor interface secured on a second side of the patient support structure, the first and second patient distractor interfaces comprising first and second, respectively, hand interface grips positioned relative to the patient support structure so a patient can grip the hand interface grips when supported by the patient support structure, the hand interface grips disposed relative to the patient support structure and configured so that a patient can apply loading vectors on the hand interface grips between the pelvis and the shoulder when the patient is supported by the patient support structure;
a patient anchoring belt adapted and configured to anchor a portion of the patient relative to the patient support structure;
a first sensor operatively coupled to the first patient distractor interface and adapted to sense patient generated the loading vectors on the first hand interface grip between the pelvis and the shoulder, the first sensor spaced from the first hand interface grip to allow a patient to apply the loading vectors on the first hand interface grip between the pelvis and the shoulder without directly contacting the first sensor;

a second sensor operatively coupled to the second patient distractor interface and adapted to sense the patient generated loading vectors on the second hand interface grip between the pelvis and the shoulder, the second sensor spaced from the second hand interface grip to allow a patient to apply the loading vectors on the second hand interface grip between the pelvis and the shoulder without directly contacting the second sensor; and a controller adapted to receive information indicative of the sensed patient generated loads.

6. The system of claim 5, wherein the controller is further adapted to control movement of at least one of the first and second patient distractor interfaces.

7. The system of claim 6, wherein the controller is further adapted to control movement of the at least one of the first and second patient distractor interfaces based on the sensed patient generated loading vectors.

8. The system of claim 5 wherein the patient support structure includes a horizontal surface.

9. The system of claim 5 further comprising a monitor adapted to provide information indicative of the patient generated loads.

\* \* \* \* \*